United States Patent
Guidi

(10) Patent No.: US 7,175,429 B2
(45) Date of Patent: Feb. 13, 2007

(54) DEVICE FOR CONTROLLING THE DISPENSING OF WAX FOR THE CREATION OF TRACINGS AND MOULDS IN DENTISTRY

(76) Inventor: Adriano Guidi, Strada Pozzo 137/M - 60029, Varano (Ancona) (IT)

( * ) Notice: Subject to any disclaimer, the term of this patent is extended or adjusted under 35 U.S.C. 154(b) by 0 days.

(21) Appl. No.: 10/477,690

(22) PCT Filed: May 16, 2001

(86) PCT No.: PCT/IB01/00850

§ 371 (c)(1),
(2), (4) Date: Dec. 8, 2005

(87) PCT Pub. No.: WO02/091942

PCT Pub. Date: Nov. 12, 2002

(65) Prior Publication Data

US 2006/0076340 A1    Apr. 13, 2006

(51) Int. Cl.
*A61C 3/00* (2006.01)
(52) U.S. Cl. ............... 433/32; 401/1; 219/229; 219/533
(58) Field of Classification Search .......... 433/32; 401/1; 219/229, 230, 533; 228/51
See application file for complete search history.

(56) References Cited

U.S. PATENT DOCUMENTS

| 3,364,577 A |   | 1/1968 | Oakleaf |
|---|---|---|---|
| 3,522,654 A | * | 8/1970 | Schoelz .................. 433/32 |
| 3,831,815 A | * | 8/1974 | Glasgow ................. 433/32 |
| 3,902,043 A | * | 8/1975 | Rogan .................... 219/242 |
| 5,073,696 A |   | 12/1991 | Patillo |
| 5,346,394 A | * | 9/1994 | DeStefanis ............. 433/32 |
| 6,255,625 B1 | * | 7/2001 | Baschenis ............... 219/227 |

FOREIGN PATENT DOCUMENTS

DE          37 32 751          3/1989

* cited by examiner

Primary Examiner—Ralph A. Lewis
(74) Attorney, Agent, or Firm—Young & Thompson

(57) ABSTRACT

A device for controlling and dispensing wax for the creation of tracings and moulds comprising a spatula-like tip (3), which is mounted on a hollow handle (4), and a control unit (1). The hollow handle (4) has internally a housing (10) containing a block of solid wax; the housing (10) communicates with a channel (12) for conveying the wax into the vicinity of the spatula-like tip; and heating elements (9) are provided around the housing (10) for the wax. Preferably, the heating temperature may be regulated by the control unit (1) via a spirally wound electrical resistance. According to an advantageous embodiment, the spatula (3) is interchangeable depending on requirements.

14 Claims, 3 Drawing Sheets

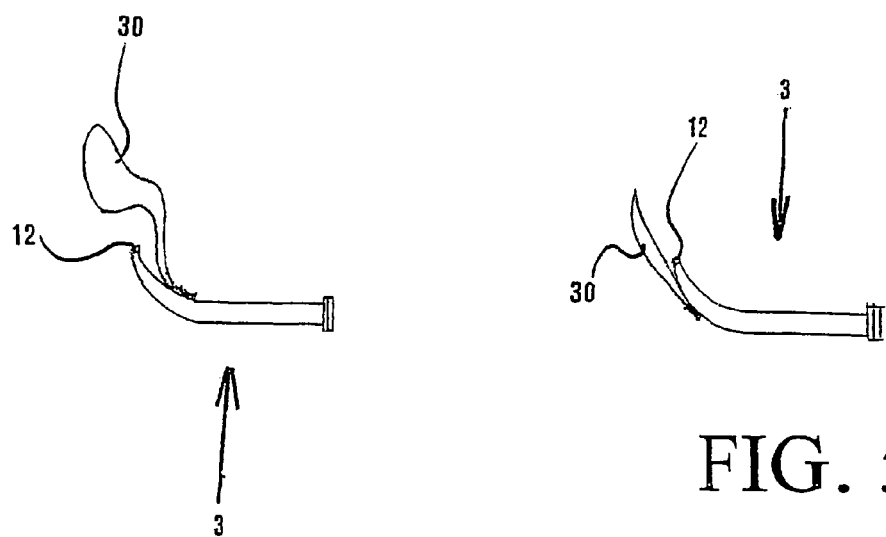
FIG. 5A
FIG. 5B
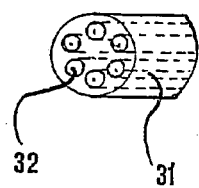
FIG. 6
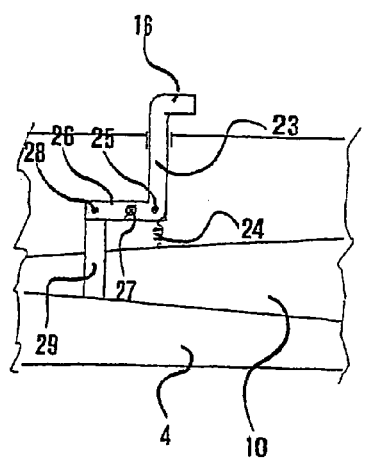
FIG. 4

DEVICE FOR CONTROLLING THE DISPENSING OF WAX FOR THE CREATION OF TRACINGS AND MOULDS IN DENTISTRY

The present invention relates to a device for controlling and dispensing wax for the creation of tracings and moulds, particularly useful in dentistry for the creation of models of natural teeth.

In dentistry, the creation of wax models of natural teeth, so as to be able to produce therefrom in the most accurate manner prostheses or implants, is very frequent. At present, the wax for these uses is generally sold in special containers, where it is in the solid or in any case in a dense state. The most common technique, currently available, for creating these moulds consists in applying the melted wax on plaster stumps where the wax cools and solidifies, thus forming the mould. This is generally performed using a metal spatula which is heated, usually over a flame, and is then immersed in the solid-wax container so as to melt a small portion thereof. An amount proportional to the dimensions of the spatula is then removed therefrom and applied, before it cools and solidifies again, onto the plaster stump where it is modelled in accordance with the design which is to be obtained. The final mould is obtained by performing a series of subsequent adding operations.

Generally, this procedure involves certain drawbacks which are not insignificant in nature. Firstly, there is the problem of performing correct heating of the tip of the spatula: in fact, insufficient heating has the effect that the quantity of wax applied is too small, with the direct consequence that the number of wax adding operations becomes excessive, while excessive heating results in too large a quantity of wax on the spatula which, owing to the small dimensions of the latter, may cause spillage of wax onto the workbench or may produce rough edges in the mould.

In order to overcome these drawbacks, an electrically heated spatula has recently been marketed. This tool comprises a power and regulating unit by means of which the temperature of the spatula is regulated using a rheostat, based on the actual requirements at the time, in order to program more efficiently the quantity of wax which may be melted in each case. The power and regulating unit then transmits the set current to a resistance which surrounds, inside a handle, an extension of the actual working tip of the spatula. This spatula reduces drastically and in a very advantageous manner the unevennesses in heating of the spatula, but is unable to solve other no less important problems.

Firstly, the wax must be removed, in this case also, from the usual containers in which it is sold. Therefore, every time it is required to remove a small quantity from them, resulting in a considerable waste of time. Moreover, despite regulation of the temperature, relatively large spillage of wax along the path between container and stump still occurs, due to the fact that the wax is transported in the liquid state on a surface, i.e. that of the spatula, which is substantially flat. Finally, as already mentioned, according to all these methods, the mould is obtained by means of subsequent additions of small quantities of wax, such that it is possible to obtain only a layered final structure instead of a single compact structure.

U.S. Pat. No. A-3,364,577 discloses an electrically heated dental wax shaping and supplying tool having quick-detachable tips. Some tips are shaping tips, while others are nozzles which both supply and shape the wax.

The present invention, which relates to a device for controlling and dispensing wax for the creation of tracings and moulds, comprising a spatula-like tip, which is mounted on a hollow handle, and a control unit, characterised in that said hollow handle has internally a housing containing a block of solid wax in the manner of a replaceable cartridge, in that said housing communicates with a channel for conveying the wax into the vicinity of said spatula-like tip and in that heating means are provided around said housing, further comprising wax metering means, characterized in that said wax metering means comprise a pushbutton which is located on the outside of the handle and which extends inside said handle so as to form a horizontal pin which is pivotably hinged with a vertical pin, in turn pivotably hinged on a fulcrum and hinged with another horizontal pin which terminates in the matter of a stopper in the bottom part of the wax housing the horizontal pin and the pushbutton being pushed against the action of a spring.

The present invention is now described in greater detail with reference to the accompanying drawings which show preferred embodiments thereof and in which:

FIG. 4 is a cross-sectional view of a detail of the spatula according to an embodiment of the present invention;

FIGS. 5A and 5B show two alternative accessories for the spatula of the device according to the present invention; and FIG. 6 shows an accessory for a preferred embodiment of the present invention.

Figure 1:
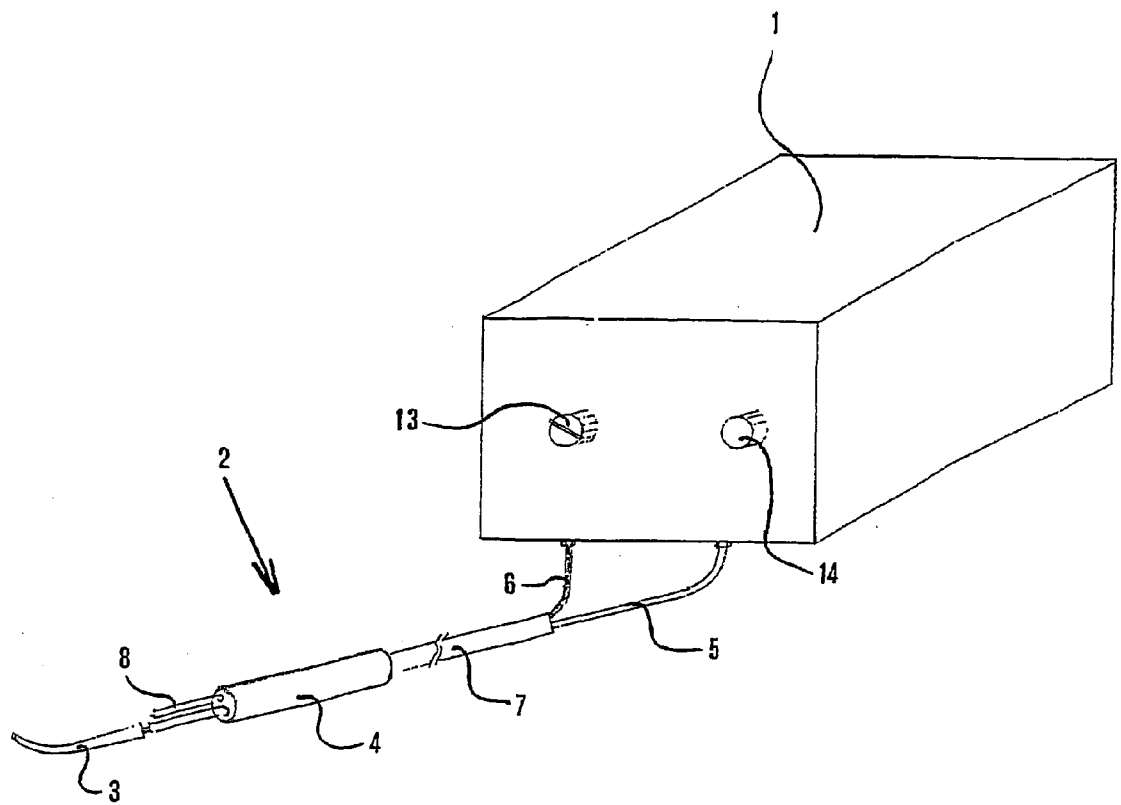
FIG. 1 is a schematic view which shows, overall, the device for controlling and dispensing wax according to the present invention.

A device for controlling and dispensing wax according to the present invention consists of a control unit 1 and a wax dispensing unit 2. The unit 2, in turn, is formed by a spatula 3 which can be manipulated by means of a handle 4. The handle 4 is connected to the control unit 1 by a small pipe 5 for compressed air and an electrical cable 6, both of which are enclosed inside a connecting sheath 7.

The compressed-air pipe 5 terminates in a nozzle 8 located in the vicinity of the spatula 3.

Figure 2:
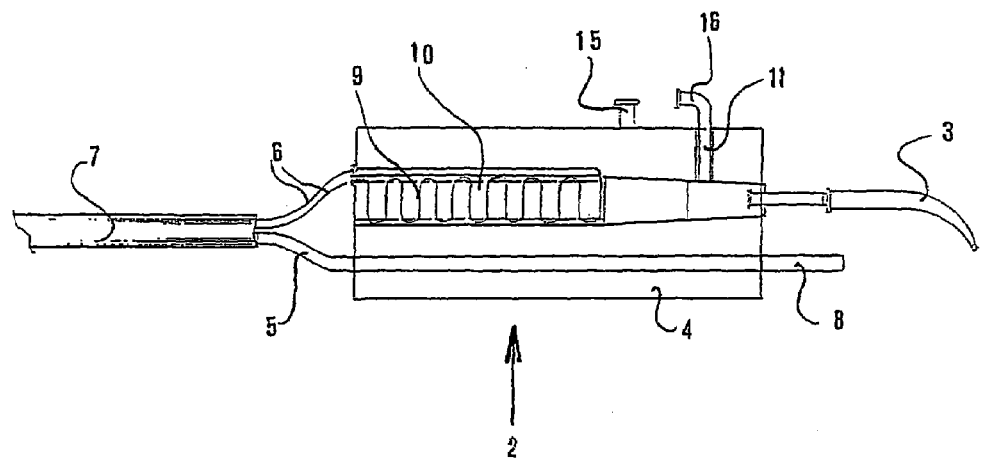
FIG. 2 is a cross-sectional view which shows the spatula of the device, according to a preferred embodiment of the present invention.

According to the embodiment illustrated in FIG. 2, the electrical cable 6 has the function of supplying power to an electrical resistance 9 which is spirally wound around a fixed housing 10 inside which a small round wax insert in a dense or solid state may be inserted—like a cartridge—for example from above via a special opening, for subsequent dispensing. Any other known heating device, for example a PTC or the like, may be provided around the housing 10 in place of a heating resistance. The bottom of the housing 10 is provided with a unit 11 for the metered supply of the melted wax, which is of the known type. The melted wax is then delivered from a special nozzle 12 of the spatula 3. Said nozzle 12 is similar to the needle of a syringe and it is possible to envisage nozzles of different sizes which are interchangeable with each other.

The control unit 1 is equipped with a knob 13 for regulating the wax melting temperature and a pressure reducer 14 for regulating the pressure and, consequently, the flow rate of air leaving the nozzle 8. The presence or not of an air flow leaving the nozzle B is determined with the aid of a pushbutton 15, while another pushbutton 16 actuates the metering unit 11.

Figure 3:
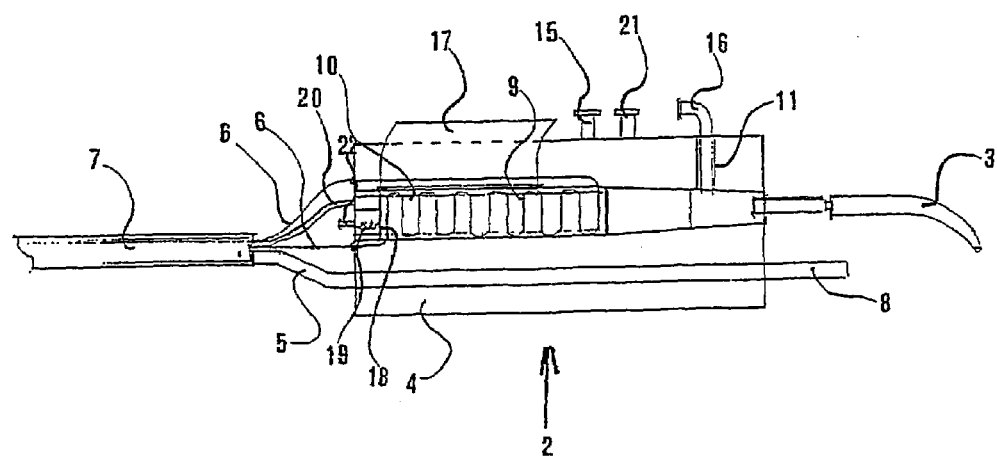
FIG. 3 shows a view—similar to one of FIG. 2—illustrating an alternative embodiment of the present invention.

The embodiment shown in FIG. 3 is an improvement to that shown in FIG. 2. According to this embodiment, the housing 10 has a small cover 17 which can be opened and allows introduction of the wax insert. Moreover, upstream of the block of wax, a piston 18 is provided, which can be axially actuated inside the housing 10 against the action of a recall spring 19, owing to a compressed-air flow supplied from an additional pipe 20. A pushbutton 21, for activating the piston 18, and a pushbutton 22, for bleeding the said piston, are also provided.

The metering unit 11, according to the present invention, is illustrated in detail in FIG. 4. The pushbutton 16 continues, inside the handle 4, in the form of a horizontal pin 23 which terminates against a spring 24, where it is pivotably hinged at 25 with a vertical pin 26. The pin 26 is in turn also pivotably hinged on a fulcrum 27 and at 28 with a second horizontal pin 29 which, in the rest condition, closes the bottom of the cartridge 10 in the manner of a stopper.

In FIGS. 5A and 5B, the spatula 3, underneath the nozzle 12, has associated therewith an accessory and interchangeable modelling plate 30 which may have different size and shapes depending on the use.

A particularly interesting embodiment of the present invention envisages a drum 31 (FIG. 6) with a plurality of axial seats 32, each able to house a small round wax insert of a type different from the others. Said drum is mounted rotatably so as to convey in each case a seat 32 to the location of the housing 10 around which the resistance 9 is wound, inside the handle 4. Obviously, the inside of the handle 4 in this case is modified so as to arrange the heating means 9—which are also modified with respect to FIGS. 2 and 3—around the seat 32 in each case being used.

When it is required to create a tracing or a mould, for example comprising one or more teeth, a wax insert of the desired type is introduced inside the housing 10. If it is required to use several different types of wax, the drum 31 may be used; it is then possible to rotate the drum until the seat 32 corresponding to the desired type of wax is conveyed to the location of the housing 10 around which the resistance 9 is wound. When it is required to change the insert, it is sufficient to rotate the drum 31 until another seat 32 is brought into position coaxial with the resistance 9, and so on.

Once the wax insert has been introduced inside the housing 10, heating of the said wax is performed by operating the special knob 13 on the unit 1: by setting a higher temperature, a greater degree of melting—and therefore a faster wax dispensing speed—is achieved, whereas a lower temperature results in a lower degree of melting and therefore a slower dispensing speed. In any case, heating of the wax is initiated, the wax thus being gradually melted.

With the embodiment illustrated in FIG. 3 it is possible to achieve particular advantages. Firstly, when the piston 18 is discharged, it is possible to open the cover 17 and introduce a wax insert into the housing 10. All this, obviously, after opening a corresponding cover situated on the outside of the handle 4.

Once heating of the wax block has started, pressing the pushbutton 21 causes compressed air to flow from the pipe 20. The compressed air applies pressure on the piston 18 until the opposing resistance of the melted wax and the recall spring 19 is overcome. At this point, the piston 18 moves and pushes the insert, thus accelerating the expulsion of the melted wax. The pressure inside the pipe 20, and therefore on the piston 18, may be regulated by means of a special pressure reducer which is also present on the control unit 1, while the compressed-air source may be the same source to which the pipe 6 is connected.

With a device such as that illustrated in FIG. 3 it is possible to expel from the nozzle 12 also wax which is not completely melted, this being particularly suitable for certain processing operations.

In any case, using the handle 4 of the dispensing unit 2, the spatula 3 is brought up to the plaster stump (or other point where the wax is to be deposited) so as to perform dispensing thereof. For this purpose, it is necessary to press the pushbutton 16 which activates the wax metering unit 11, keeping it pressed for the whole time during which wax is to be expelled and releasing it in order to stop dispensing.

Pushing the pushbutton 16 moves the horizontal pin 23 of the unit 11 in the same direction, against the action of the spring 24. By means of the spring 24 it is possible to graduate more effectively the force applied to the pushbutton and correspondingly adjust more finely the displacement of the pin 23. The pivot 25 transmits the movement to the vertical pin 26 which, in turn and by means of the fulcrum 27 and the pivot 28, moves the horizontal pin 29 in the opposite direction to the pin 23. The said pin 29, moving, leaves open a passage on the bottom of the housing, which is wider the greater the thrust exerted on the pushbutton 16, in the manner of a stopper. In this way, the wax is able to flow towards the outlet at a flow rate which is greater the wider the passage which is left open on the bottom of the housing 10, i.e. the greater the thrust exerted on the pushbutton 16.

In this way, the wax is able to emerge from the nozzle 12, so as to be spread and modelled. The plate 30 of the spatula 3, which is present as an optional accessory underneath the nozzle 12, allows modelling to be performed more efficiently.

A small, low-pressure, compressed-air flow may be used in order to cause more rapid solidification of the wax, as it is gradually applied and modelled. The control unit 1 may, in fact, be connected to a compressed-air circuit (for example to a cylinder or a compressor). The flow rate of the air is regulated by means of the pressure reducer 14 which is present on the unit 1. The air flows through the pipe 5 and emerges at the desired flow rate from the nozzle 8, striking the wax being supplied. In this way it is possible to obtain more rapid re-solidification of the wax, so as to prevent wastage of material or the creation of an unwanted surrounding edge on the tracing or model being prepared.

When operation is to be interrupted, the pushbutton 16 is first released. In this way, the spring 24 pushes the pin 23 and the pushbutton 16 itself outwards. The pin 23 thus brings the pin 26 and the pin 29 into the rest position shown in FIG. 4, closing off, in the manner of a stopper, the bottom of the housing 10 so as to interrupt immediately the outflow of wax. The heating and the compressed air is then suspended by setting the knob 13 to "0" and discharging the pressure reducers.

If the device according to the embodiment shown in FIG. 3 is being used, the pushbutton 22 is also pressed in order to bleed the compressed air upstream of the piston 18, discharging it. The latter is then brought into the rest position by the recall spring 19.

From the above description it is apparent that the device for controlling and dispensing wax according to the present invention is able to achieve advantages which were not even imaginable hitherto in this technical sector. In fact, the wax is dispensed such that attention can be focussed solely on the creation of the tracing or mould, without wasting time in melting and removing the quantity which is required each time. As a result, it is possible to operate not only more rapidly than before, but also under much cleaner conditions, without wastage of material.

Moreover, owing to the combination of the metering unit 11 with the heating device 9, it is possible to achieve continuous and uniform processing, resulting in a product which is of much higher quality compared to the present layered products. A further improvement consists in the additional flow of drying air, which prevents the melted wax from running and therefore allows more precise modelling. Finally, due to the design of the assembly consisting of spatula 3 with the nozzle 12 and the modelling plates 30, it is possible to provide several interchangeable spatulas 3, with a considerable increase in versatility. Finally, the use of a drum such as that indicated by 31 in FIG. 6 ensures that several different types of wax may be used with the maximum rapidity during the same operation using a single device. Basically, with the device according to the present invention it is possible gain full control over the wax, from the start to the end of its processing path, thereby resulting in a revolution in the dentistry sector which is comparable to the transition from a quill pin to a fountain pen.

It is understood that the present invention may be subject to other modifications and variations, without thereby departing from the protective scope thereof. In particular, the systems for regulating the flow rate of the air and wax may be different from those described, and likewise the heating device may be of any known type. Furthermore, the piston 18 may be actuated in a manner different from that described. Finally, all the controls have been illustrated as being of the mechanical type, but it is obvious that they may be of any other type, such as electronic for example, and that the pushbuttons located on the handle 4 may also be grouped together on the control unit 1.

The invention claimed is:

1. Device for controlling and dispensing wax for the creation of tracings and moulds, comprising a spatula-like tip (3), which is mounted on a hollow handle (4), and a control unit (1), wherein said hollow handle (4) has internally a housing (10) containing a block of solid wax in the manner of a replaceable cartridge, wherein said housing (10) communicates with a channel (12) for conveying the wax into the vicinity of said spatula-like tip (3) and wherein heating means (9) are provided around said housing (10), further comprising wax metering means (11), wherein said wax metering means (11) comprise a pushbutton (16) which is located on the outside of the handle (4) and which extends inside said handle (4) so as to form a horizontal pin (23) which is pivotably hinged with a vertical pin (21), in turn pivotably hinged on a fulcrum (27) and hinged with another horizontal pin (29) which terminates in the manner of a stopper in the bottom part of the wax housing (10), the horizontal pin (23) and the pushbutton (16) being pushed against the action of a spring (24).

2. Device according to claim 1, characterised in that the spatula (3) is formed by a small pipe which is similar to a syringe needle terminating in a nozzle (12).

3. Device according to claim 1, characterised in that means for rapid replacement of said block of solid wax are associated therewith.

4. Device according to claim 3, characterised in that said means consist of a rotating drum (31), which has a plurality of axial seats (32) for a corresponding number of wax inserts and which is mounted so that, when said drum (31) is rotated, said seats (32) are located one at a time corresponding with the heating means (9).

5. Device according to claim 1, characterised in that said wax metering means also comprise a piston (18) which is located upstream of the wax insert.

6. Device according to claim 5, characterised in that said piston (18) comprises a recall spring.

7. Device according to claim 5, characterised in that said piston is actuated by compressed air.

8. Device according to claim 7, characterised in that means (22) for bleeding the compressed air are associated with said piston (18).

9. Device according to claim 1, characterised in that it also comprises means (14; 5; 8) for cooling the wax.

10. Device according to claim 9, characterised in that said cooling means comprise a compressed-air flow coming from a compressed-air source which supplies the control unit (1), there being provided in said unit (1) a pressure reducer (14) for regulating the pressure of the air which is conveyed by means of a line (5) to a nozzle (8) which is located in the vicinity of the spatula (3).

11. Device as in claim 10, characterised in that said compressed-air source is a cylinder.

12. Device according to claim 10, characterised in that said compressed-air source is a compressor.

13. Device according to claim 10, characterised in that the same compressed-air source supplies the cooling circuit and the circuit actuating the piston (18).

14. Use of a device according to claim 1 in dentistry.

* * * * *